United States Patent
Weigum et al.

[19]

[11] Patent Number: 5,827,284

[45] Date of Patent: Oct. 27, 1998

[54] DEVICE FOR EXTERNALLY SECURING FRACTURES

[75] Inventors: Hans Weigum, Neiderdorf; Oscar E. Illi, Schwerzenbach, both of Switzerland

[73] Assignee: Hans Weigum, Switzerland

[21] Appl. No.: 793,986

[22] PCT Filed: Sep. 4, 1995

[86] PCT No.: PCT/CH95/00189

§ 371 Date: May 19, 1997

§ 102(e) Date: May 19, 1997

[87] PCT Pub. No.: WO96/07362

PCT Pub. Date: Mar. 14, 1996

[30] Foreign Application Priority Data

Sep. 7, 1994 [CH] Switzerland .............. 2737/94

[51] Int. Cl.[6] .............................. A61B 17/64
[52] U.S. Cl. .............................. 606/59; 606/54
[58] Field of Search .............. 606/54, 55, 56, 606/57, 58, 59, 72, 73

[56] References Cited

U.S. PATENT DOCUMENTS

| 2,406,987 | 9/1946 | Anderson | 606/59 |
|---|---|---|---|
| 4,271,832 | 6/1981 | Evans et al. | 606/59 |
| 4,978,348 | 12/1990 | Ilizarov | 606/57 |

FOREIGN PATENT DOCUMENTS

| 0517939 | 12/1992 | European Pat. Off. . |
|---|---|---|
| 0524441 | 1/1993 | European Pat. Off. . |
| 9005149 | 8/1990 | Germany . |
| 8801488 | 3/1988 | WIPO . |

OTHER PUBLICATIONS

F. Behrens and K. Searls, "External Fixation of the Tibia" published in *The Journal of Bone and Joint Surgery*, vol. 68–B, No. 2 (Mar. 1986), pp. 246–254.

*Primary Examiner*—Guy V. Tucker
*Attorney, Agent, or Firm*—Speckman Pauley Petersen & Fejer

[57] ABSTRACT

A device for securing fractures, the device having at least one traction/compression rod, a plurality of bone screws and clamps wherein the clamps have a threaded tubular supporting member. The supporting member is pierced by two diametric, axially staggered through-holes through which the traction/compression rod or the bone screw passes and is therein clamped. The bone screw is adjustably clamped by a supporting ring with a conical outer surface and a mating ring thereon with a conical inner surface and a clamping ring. The traction/compression rod is held only by a clamping ring and thereby provides a particularly economical system which is highly adaptable, easy to use, and particularly suitable for use by paramedical staff.

13 Claims, 6 Drawing Sheets

DEVICE FOR EXTERNALLY SECURING FRACTURES

BACKGROUND OF THE INVENTION

This application is filed under 35 USC 371 based on PCT/CH95/00189, filed Sep. 4, 1995.

This invention relates to a device for external fixation of fractures, in particular of the extremities and the pelvis, having at least a traction/compression rod as well as several bone screws, such as Schanz screws, or bone pegs, such as Steinmann pins, and connecting clamps for making the connection between the bone screws and the force-transmitting traction/compression rod.

Open, infected fractures as well as comminuted fractures are treated surgically with this device, which in technical language is mainly referred to as a fixateur extern. When using this device it is not necessary to expose the bone in the fracture area, in contrast to internal fixation by implants. The considerably simplified application permits the employment of such a device also by paramedics, such as emergency technicians and military corpsmen. The main area of employment of the device for the external fixation of fractures is essentially in war and catastrophic medical treatment and in accident surgery as a quick, temporary or definitive treatment. The capability of stressing a bone fixed in this manner immediately following the application by surgery is so great, that a patient can then be released from treatment immediately. This is an economically important factor in many countries with insufficient medical care and an acute lack of hospital beds. It is apparent that economical considerations are of eminent importance when purchasing such devices.

A conventional device for external fixation of fractures is taught by EP-A-O 524 441, which comprises connecting clamps which encloses a cylindrical support body, with two axially offset through-openings in the form of eccentric recesses in the support body. These recesses are dimensioned to correspond to the diameter of the bone screws or the traction/compression rod. The traction/compression rod or the bone screws are held in the support body by retaining sleeves, on which a corresponding nut is indirectly or directly forced.

Examining the latest developments in this field it is noted that most of the new developments lead in the direction of perfection with increasingly accurate adaptation possibilities and expensive accessories. One of the most expensive parts of the entire device is the connecting clamp which is, used to provide the connection between a bone screw and the force-transmitting traction/compression rod. A widely used connecting clamp can be seen at least in a suggested manner in the representation of FIG. 1. Such a clamp has a U-shaped holding element with a bore penetrating through both cheeks and a block with a through-bore of the same dimensions seated between the two cheeks. The traction/compression rod is guided through the through-bore and is clamped by displacing the block in relation to the U-shaped body with a screw. The clamp includes a pair of clamping cheeks which are pressed together by a further screw. Furthermore, the angular position of the two cheeks in relation to each other is secured and the relative angular position of the clamping cheeks is fixed in place on the body of the clamp. All elements of the clamp make high demands on their manufacture, must be produced with extreme precision and accordingly are expensive and correspondingly sensitive to overloads and damage.

SUMMARY OF THE INVENTION

It is therefore one object of this invention to provide a device of the type mentioned above, which has a connecting clamp that can be produced at considerably less cost and that requires less precision but yet has a high degree of adaptability regarding the angular position of the different parts extending with respect to each other which must be connected.

This object is achieved with a device of the type mentioned above, having features described in this specification.

When producing small batches or in production with the simplest possible tools, the connecting clamp advantageously comprises a support body which can be made from a section of a threaded pipe. It is possible to produce all other elements of the connecting clamp as simple parts turned on a lathe. The pipe-shaped support body of the connecting clamp can also be produced as a cast element, which results in a particularly economical production if a correspondingly large number of pieces are produced.

Further advantageous embodiments of this invention are represented in the drawings and will be explained in the following description.

BRIEF DESCRIPTION OF THE DRAWINGS

Two preferred embodiments of this invention are represented in the drawings.

DESCRIPTION OF PREFERRED EMBODIMENTS

No mention is made of the purely surgical application of a device for external fixation of fractures. Reference is made to an article by F. Behrens and K. Searls, "External Fixation of the Tibia" published in the British Journal of Bone and Joint Surgery, 68–93 (1986), pages 246 to 254.

A connection between bone fragments and a fixing device is generally made with either bone screws or bone pegs.

However, for the sake of simplicity only bone screws will be mentioned here, which are used more often than bone pegs. Often Schanz screws are used as bone screws.

Figure 1:
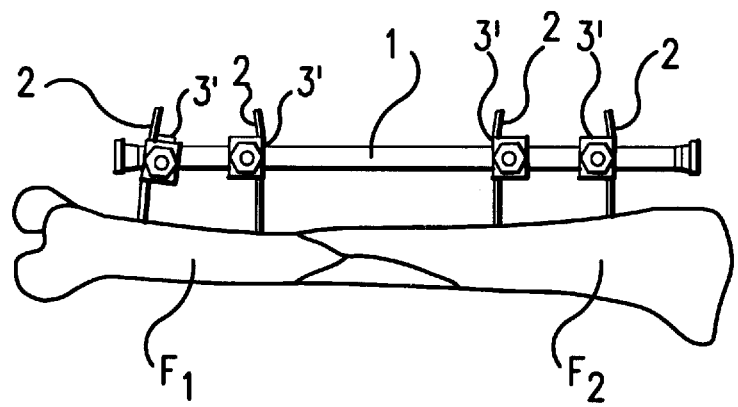
FIG. 1 is a front view of a conventional device for external fixation of fractures using conventional connecting clamps.
Figure 2:
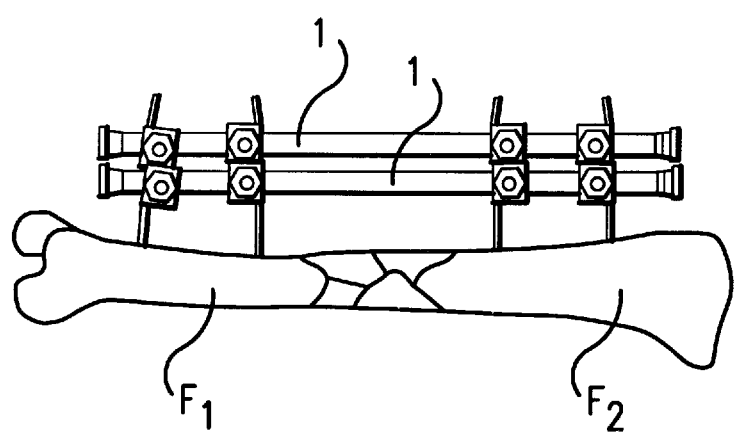
FIG. 2 is a front view of the same device as shown in FIG. 1, but in a somewhat more complex application.

As shown in FIGS. 1 and 2 two bone fragments F1 and F2 are stabilized with respect to each other by means of a known device. A traction/compression rod 1 extends approximately parallel to a direction of extension of the bone to be fixated, while the bone screws 2 are screwed into the bone approximately perpendicularly with respect to the direction of its extension. On one end the connecting clamps 3 are penetrated by the traction/compression rod 1 and on the other end the connecting clamps 3 clampingly hold the bone screws 2. In this case respectively two bone screws 2 are inserted into each of the two main bone fragments F1 and F2. This is necessary for exact fixation in place and axial stabilization in relation to the traction/compression rod 1. Different conditions may make it necessary to make more than one traction/compression rod 1 available for fixating a fracture. In this case two or even three traction/compression rods 1 can be fastened on the same bone screws 2, for example.

However, the traction/compression rods 1 can also be connected with the bone fragments F1 and F2 by means of different bone screws 2. In such cases connecting rods can also be attached between the traction/compression rods 1, which in turn are also held by means of the connecting clamps 3.

Figure 3:
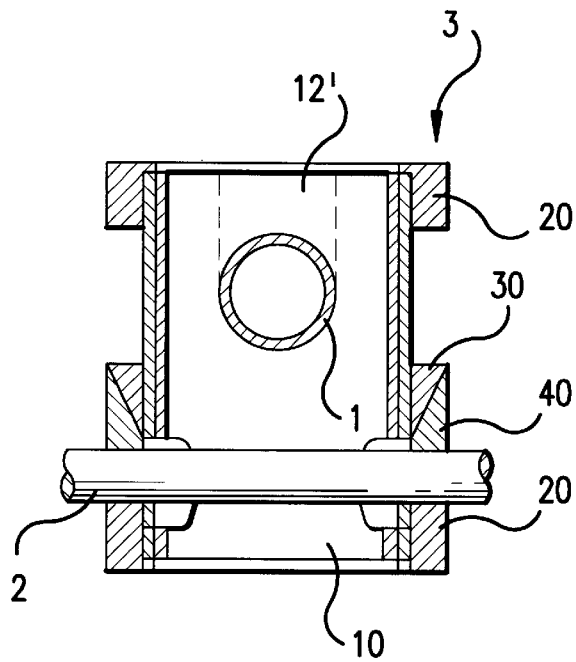
FIG. 3 is a partial sectional view of a preferred embodiment of a connecting clamp in accordance with this invention in axial longitudinal section parallel with a direction of extension of a bone screw.
Figure 4:
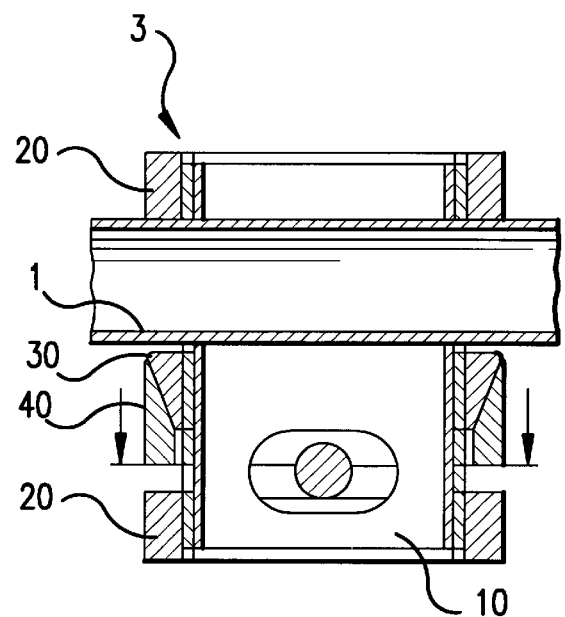
FIG. 4 is a sectional view taken in a direction of extension of a traction/compression rod.
Figure 5:
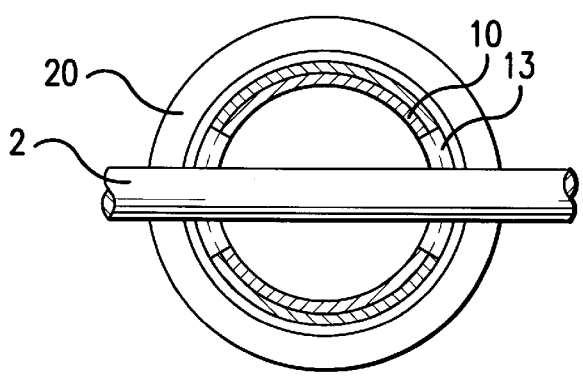
FIG. 5 is a sectional view taken perpendicularly with respect to the longitudinal axis of the connecting clamp in a penetration plane of the bone screw.

In the drawings the connecting clamps 3 representing the prior art are indicated by element reference numeral 3' in FIGS. 1 and 2, while the novel connecting clamps in accordance with the invention are identified as element reference numeral 3, as shown in FIGS. 3 to 5.

As shown in FIGS. 1 and 2, the connecting clamps 3' must be able to hold the traction/compression rods 1 on the one end and on the other end the bone screws 2 in a fixed manner. The connecting clamp 3 comprises a support body 10 and different rings arranged on the support body 10. The support body 10 has two through-openings 12 and 13, which are offset with respect to each other in the axial direction. The diametrically extending through-opening 12 is a cylindrical bore of such dimensions that the force-transmitting traction/compression rod 1 can pass through the bore with relatively little play. Accordingly, the freedom of movement of the support body 10 with respect to the traction/compression rod 1 is limited to a displacement of the support body 10 in the direction of the longitudinal axis of the traction/compression rod 1 and to a rotation around the longitudinal axis of the traction/compression rod 1.

Since the traction/compression rod 1 transmits both traction and compression loads when used, it is generally identified as a traction/compression rod.

Figure 6:
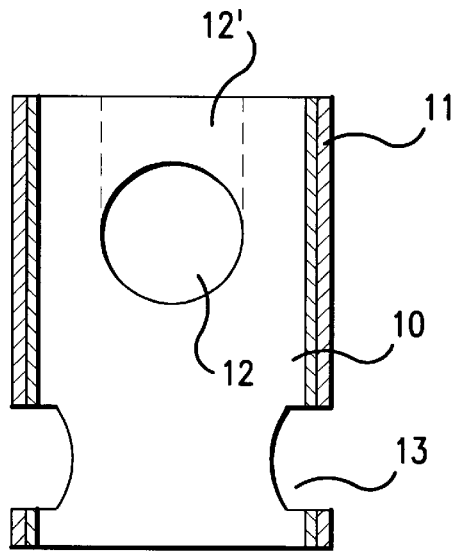
FIGS. 6 to 8 show two longitudinal views and one cross sectional view taken through a support body of one embodiment of the connecting clamp.
Figure 7:
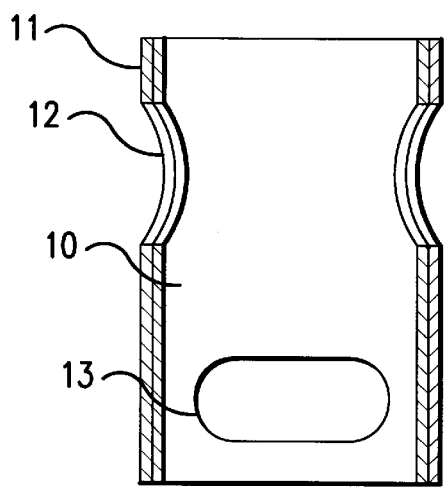
Figure 8:
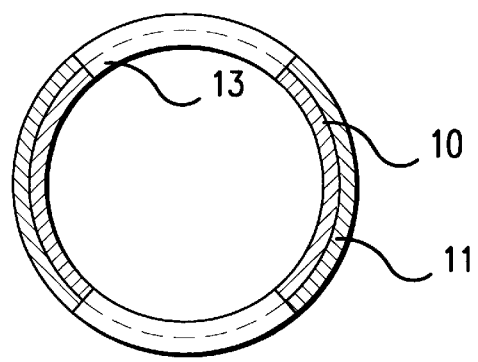
Figure 9:
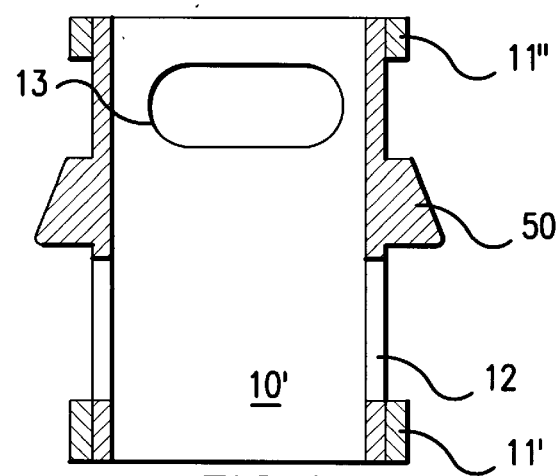
FIGS. 9 to 11 show two longitudinal views and one front view of a support body of another embodiment of the connecting clamp.
Figure 10:
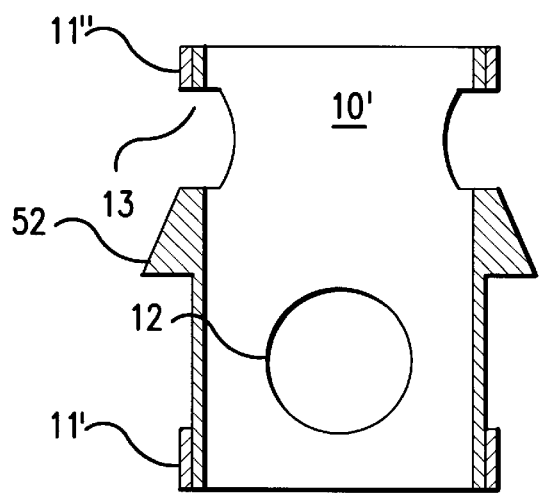
Figure 11:
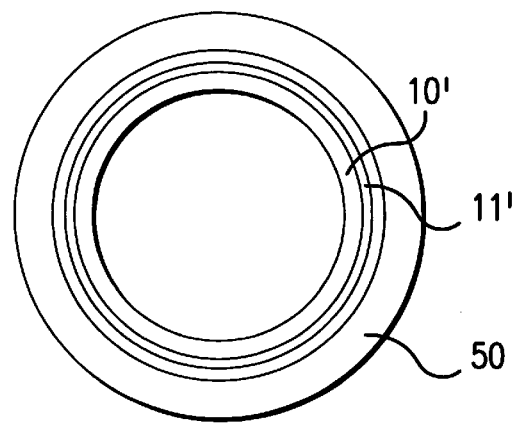
Figure 12:
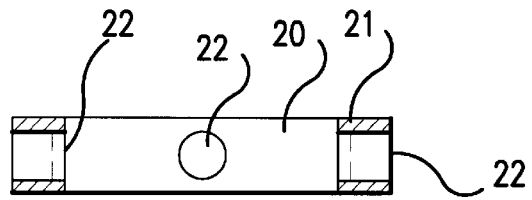
FIG. 12 shows a cross section of a clamping ring.
Figure 13:
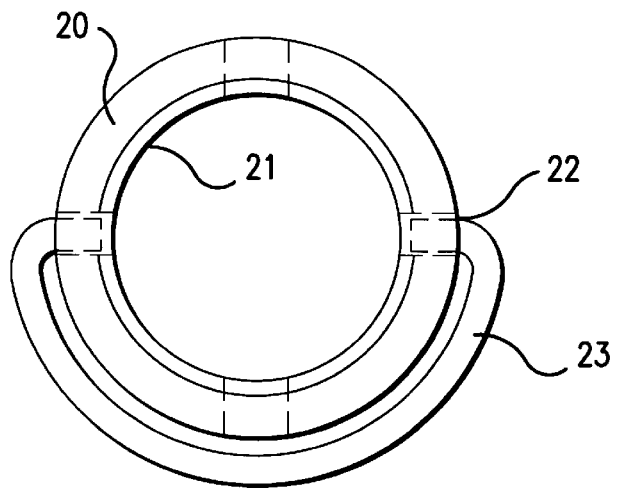
FIG. 13 is a top view of the clamping ring shown in FIG. 12.
Figure 14:
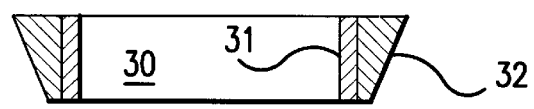
FIG. 14 is an axial sectional view taken through a support ring.
Figure 15:
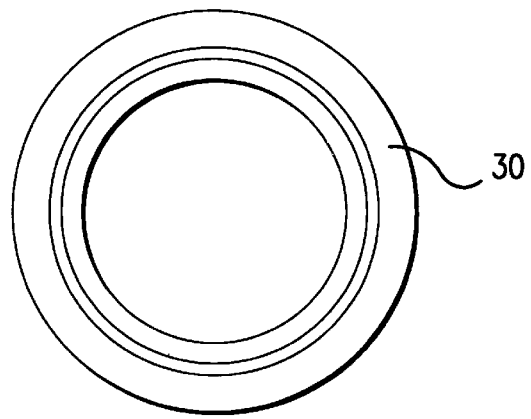
FIG. 15 is a top view of the support ring shown in FIG. 14.
Figure 16:
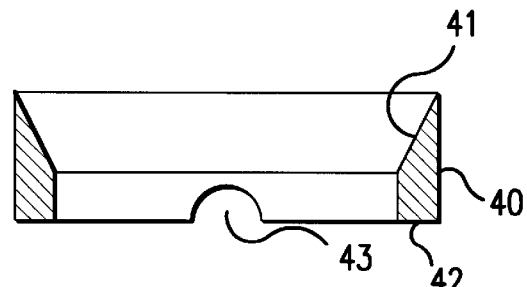
FIG. 16 is a sectional view of a clamping ring.
Figure 17:
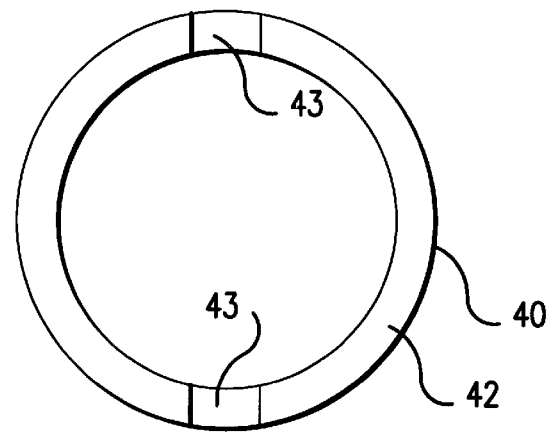
FIG. 17 is a bottom view of the clamping ring shown in FIG. 16.

As shown in FIGS. 6 to 8, the support body 10 can be manufactured from a threaded pipe section. In that case the pipe-shaped support body 10 has an exterior thread 11 extending over the entire length. The traction/compression rod 1 is fixed in the support body 10 in the simplest way with a clamping ring 20 with an interior thread 21 rotated on the exterior thread 11. Such a clamping ring 20 has engagement surfaces for a screw tool. In one preferred embodiment engagement surfaces are formed as radial bores 22. A clamping ring 20 which has bores as engagement surfaces is suitable, for example, for being tightened by means of a hook wrench. In a special embodiment two bores, which are situated diametrically opposite each other, can also be used as receptacles for a releasable hoop. This hoop, which is pivotally connected with the clamping ring 20, permits rapid fastening of the clamping ring 20 on the support body 10 without the use of tools, and sufficient force for achieving clamping can thereby be transmitted, which is sufficient for a temporary positional fixation. For the final definitive fixation either a pipe-shaped key can be pushed over the hoop 23, which uses the latter for transferring the moment to the clamping ring 20, or the hoop 23 is removed and the clamping ring 20 is tightened with the hook wrench. The clamping ring 20 can of course also be equipped with flat engagement surfaces on the exterior, so that the clamping ring 20 can be tightened in a way similar to a nut, for example with the aid of an open-end wrench. Other embodiments, which are matched to appropriate known tools, can of course also be incorporated.

A second through-opening 13 passing diametrically through the support body 10 is used for passing a bone screw 2 through the support body 10. While the traction/compression rod 1 is maintained interlockingly in the support body 10, this does not apply to passing the bone screw 2 through the support body 10. Instead, the bone screw 2 must have sufficient freedom of movement for providing the required angular adaptation. Accordingly, the through-opening 13 for the bone screw 2 is shaped more like a window. In one embodiment the through-opening 13 is an elongated hole. Here, clamping of the bone screw 2 does not take place between a second clamping ring 20 and the support body 10, but between a second clamping ring 20 and an adapter ring 40.

A support ring 30 is screwed on the exterior thread 11 in the area between the two through-holes 12 and 13, which extend axially offset and skewed perpendicularly with respect to each other. The support ring 30 has an interior thread 31, which engages with the exterior thread 11 of the support body 10 and which is permanently fixed against relative rotation after it is mounted. The radial exterior surface of the support ring 30 is preferably conically designed. An adapter ring 40, which has an appropriately inclined conical interior surface 43, rests on the conical exterior surface of the support ring 30. The adapter ring 40 represents a conditionally movable clamping cheek. The bone screw 2 is held between this clamping cheek and a second clamping ring 20. This fastening is advantageously designed in such a way that the bone screw 2 is held not only frictionally connected, but also interlockingly. The adapter ring 40 accordingly has pairs of open recesses 43 placed diametrically opposite each other on a flat front face 42. The depth of various recesses 43 distributed over a circumference can be different, corresponding to the diameters of the bone screws 2 to be clamped. The diameter of customary bone screws 2 varies between 3 and 5 millimeters. The shape of the open recesses 43 can be semicircular, semi-oval or can have the shape of a triangular notch in order to increase the clamping effect.

While the embodiment in accordance with the general drawings of FIGS. 3 to 5 comprises individual elements in accordance with FIGS. 6 to 8 and 12 to 17, FIGS. 9 to 11 represent a variant of a support body 10', which is not of a threaded pipe, but can be turned by means of a lathe from a thick-walled pipe or can even advantageously be made as a cast element. The support body 10' has a collar 50, which is connected in one piece with the support body 10' and corresponds in appearance and in function to the support ring 30. The collar 50 also has a corresponding conically extending radial exterior surface 52. This in turn is used as a support surface for the conical interior surface 41 of the adapter ring 40. Based on production considerations, the exterior thread on the support body 10 may not extend over its entire length, but may only be provided where functionally required in the two end areas. These threaded sections have accordingly been identified by element reference numerals 11' and 11".

In principle it is also possible to design the clamping between the clamping ring 20 and the adapter ring 40 without the conical design of the contact surfaces, oriented toward each other, of the support ring 30 and adapter ring 40. However, this would require an increased production outlay and demand a greater tightening force of the elements to be screwed together. But either is undesirable, so that the embodiment with conical contact surfaces is preferred. The conicity of the contact surfaces is a question of optimization.

One advantage of the device in accordance with this invention is that it makes considerably fewer demands on the material rigidity and the accuracy of production, without reductions being required in the quality of the fixation of the fractured parts with respect to each other. Also, the solution in accordance with this invention is considerably more tolerant of damage and excess stresses occurring in the course of use, when compared to other known systems.

The construction also permits a multitude of preferred embodiments. Thus, instead of the diametric, cylindrical bore 12, the support body 10 can have a pair of open slits 12', as alternatively indicated by dash-dotted lines in FIGS. 3 and 6. Thus the entire connecting clamp 3 can be laterally attached to the rod instead of being pushed on the traction/compression rod 1. At times this is desirable for surgical reasons, if it appears that a further bone screw 2 is required for stabilizing the fragments F1 and F2.

Figure 18:
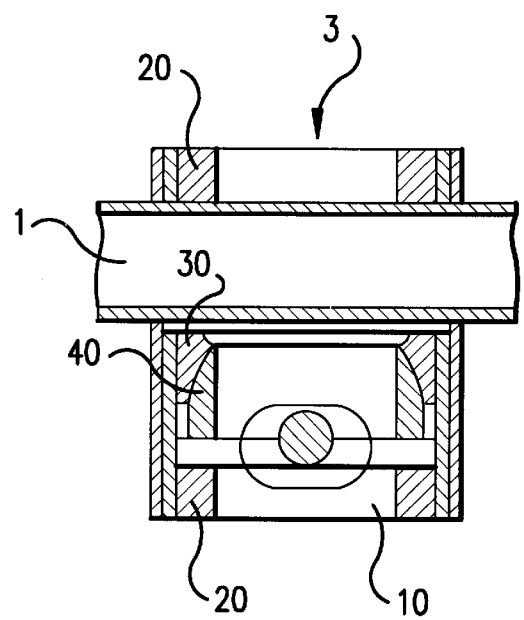
FIG. 18 is a partial sectional view of a connecting clamp with clamping rings disposed in an interior.

While in the embodiments described above the support body 10 has exterior threads and the conical support ring is placed on the exterior, this can of course also be designed in reverse, in that the thread is disposed in the interior and the support ring 30 also projects inward. The clamping rings 20 then have an exterior thread and can be screwed pin-like into the support body 10. The clamping rings 20 then must have an interior actuation, such as an interior hexagonal or square or torx actuation. This embodiment provides a particularly space-saving solution. This embodiment is shown as a system in FIG. 18. The clamping rings 20 are shown to have a hexagonal socket.

We claim:

1. In a device for external fixation of a fracture of a bone, the device having a traction/compression rod (1), a plurality of bone screws (2), a plurality of connecting clamps (3) for connecting the bone screws (2) and the traction/compression rod (1), wherein each of the connecting clamps (3) has at least one thread (11, 11', 11") and a support body (10, 10') with at least two axially offset through-openings (12, 13) passing through the support body (10, 10'), wherein widths of the through-openings (12, 13) are adapted to the traction/compression rod (1) passing through one of the through-openings (12, 13) and one of the bone screws (2) passing through another of the through-openings (12, 13), the improvement comprising: each of the connecting clamps (3) comprising the support body (10, 10') being pip-shaped and having at least two clamping rings (20), each of the clamping rings (20) being mateably engageable with the thread on the support body (10, 10') for respective fixed clamping of the traction/compression rod (1) and the bone screw (2) with the support body (10, 10') of the connecting clamp (3).

2. In the device in accordance with claim 1, the support body (10, 10') is constructed from a section of a threaded pipe.

3. In the device in accordance with claim 2, further comprising a support ring (30) fastened between the through-bores (12, 13), an adapter ring (40) resting on the support ring (30) and acting as a first clamping cheek for one of the bone screws (2), and a second clamping cheek formed by one of the clamping rings (20).

4. In the device in accordance with claim 3, wherein the support ring (30) and the adapter ring (40) have contact surfaces (32, 41) oriented toward each other.

5. In the device in accordance with claim 3, wherein at a front face remote from the support ring (30) the adapter ring (40) has a plurality of open recesses (43) for interlocked seating of one of the bone screws (2).

6. In the device in accordance with claim 5, the open recesses (43) accommodate different diameters of the bone screws.

7. In the device in accordance with claim 1, wherein the support body (10, 10') has the thread (11', 11") only at two end portions of the support body (10, 10'), and a collar (50) is positioned between the through-openings (12, 13), the collar (50) supports an adapter ring (40) which is used as a clamping cheek for one of the bone screws (2), and a second clamping cheek is formed by one of the clamping rings (20).

8. In the device in accordance with claim 7, wherein the collar (50) forms a support for the adapter ring (40) and the supported adapter ring (40) and the collar (50) have contact surfaces (41, 52) oriented toward each other.

9. In the device in accordance with claim 1, wherein the clamping rings (20) have engagement surfaces for accommodating a screw tool.

10. In the device in accordance with claim 9, wherein the engagement surfaces are formed as bores (22) which are used as engagement surfaces for engaging a hook wrench.

11. In the device in accordance with claim 10, wherein the bores (22) are located approximately diametrically opposite with respect to each other and a releasable hoop (23) is positioned within the bores (22).

12. In the device in accordance with claim 9, wherein the engagement surfaces are flat.

13. In the device in accordance with claim 9, wherein the clamping rings (20) each have an exterior thread and the engagement surfaces form an interior polygon socket for accommodating a socket wrench.

* * * * *